United States Patent
Chu et al.

(10) Patent No.: US 11,328,791 B2
(45) Date of Patent: May 10, 2022

(54) METHOD FOR DETERMINING THE RISK OF DEVELOPING ACUTE KIDNEY INJURY IN A HUMAN SUBJECT WITH ACUTE MYOCARDIAL INFARCTION AND INHIBITING SUCH DEVELOPMENT

(71) Applicants: Chang Gung University, Taoyuan (TW); Chang Gung Memorial Hospital, Linkou, Taoyuan (TW)

(72) Inventors: Pao-Hsien Chu, Taoyuan (TW); Yu-Sun Chang, New Taipei (TW); Chia-Chun Chen, Taoyuan (TW); Pei-Chun Fan, Taoyuan (TW)

(73) Assignees: Chang Gung University, Taoyuan (TW); Chang Gung Memorial Hospital, Linkou, Taoyuan (TW)

( * ) Notice: Subject to any disclaimer, the term of this patent is extended or adjusted under 35 U.S.C. 154(b) by 663 days.

(21) Appl. No.: 16/138,449

(22) Filed: Sep. 21, 2018

(65) Prior Publication Data
US 2019/0119751 A1   Apr. 25, 2019

(30) Foreign Application Priority Data
Oct. 23, 2017   (TW) .................. 106136303

(51) Int. Cl.
| C12Q 1/68 | (2018.01) |
| G16B 20/00 | (2019.01) |
| G16B 40/00 | (2019.01) |
| C12Q 1/6883 | (2018.01) |
| G16B 25/10 | (2019.01) |
| G16B 5/20 | (2019.01) |

(52) U.S. Cl.
CPC ............ *G16B 20/00* (2019.02); *G16B 40/00* (2019.02); *C12Q 1/6883* (2013.01); *C12Q 2600/106* (2013.01); *C12Q 2600/118* (2013.01); *C12Q 2600/158* (2013.01); *C12Q 2600/178* (2013.01); *G16B 5/20* (2019.02); *G16B 25/10* (2019.02)

(58) Field of Classification Search
None
See application file for complete search history.

(56) References Cited

PUBLICATIONS

Fan etal; Human Genomics (2016)10:29; pp. 1-13.*

* cited by examiner

*Primary Examiner* — Jehanne S Sitton
(74) *Attorney, Agent, or Firm* — Schwegman Lundberg & Woessner, P.A.

(57) ABSTRACT

A method for determining a human subject's risk of developing acute kidney injury (AKI) from acute myocardial infarction (AMI) includes: obtaining a blood sample; determining at least two miRNA expression levels therein, which are selected from miR-23a-3p, miR-24-3p, and miR-145-5p expression levels; calculating probability of developing AKI from AMI based on the at least two miRNA expression levels and a logistic regression model; comparing the probability with a predetermined standard; and determining that the human subject is at the risk of developing AKI when the probability is higher than the predetermined standard. A composition may be administered to the human subject for inhibiting development of AKI, if any.

10 Claims, No Drawings

METHOD FOR DETERMINING THE RISK OF DEVELOPING ACUTE KIDNEY INJURY IN A HUMAN SUBJECT WITH ACUTE MYOCARDIAL INFARCTION AND INHIBITING SUCH DEVELOPMENT

CROSS-REFERENCE TO RELATED APPLICATION

This application claims priority of Taiwanese Patent Application No. 106136303, filed on Oct. 23, 2017.

FIELD

This disclosure relates to a method for determining the risk of developing acute kidney injury from acute myocardial infarction and inhibiting such development. Particularly, this disclosure relates to a method for determining the risk of developing acute kidney injury from acute myocardial infarction and inhibiting such development, which uses at least two biomarkers selected from miR-23a-3p, miR-24-3p, and miR-145-5p.

BACKGROUND

Acute kidney injury (AKI) might be induced by various serious diseases, and results in rapid failure of kidney function, leading to numerous complications such as fluid overload, electrolyte imbalance, metabolic acidosis, uremia, and so forth. In recent years, the concept of cardiorenal syndrome has been proposed, gradually bringing people's attention to the AKI induced by acute coronary syndrome (ACS) which includes acute myocardial infarction (AMI). AMI arises from myocardial ischemia and myocardial injury which are caused by interruption of myocardial blood flow. It has been reported that approximately 12% to 36% of patients with AMI develop AKI in about 2 to 7 days.

The clinical diagnosis of AKI is generally conducted by detecting abnormal elevation in the serum creatinine level. However, when a patient is diagnosed as developing AKI, the best timing for treatment usually has passed. If the risk of developing AKI can be timely determined, intravascular volume expansion may be conducted or a vasopressor may be applied in advance, and iatrogenic nephrotoxicity may be prevented. Therefore, researchers in the relevant field endeavor to look for a reliable biomarker that can be used to predict the occurrence of AKI, especially the AKI attributed to AMI.

Several studies attempted to use neutrophil gelatinase-associated lipocalin (NGAL) in serum and urine as a biomarker for predicting the occurrence of AKI. However, it was found that NGAL in serum might be susceptible to numerous coexisting variables, including chronic kidney diseases, chronic hypertension, systemic infections, inflammatory conditions, anemia, hypoxia, and malignancies. Further, since NGAL was found to be expressed in atherosclerotic plaques and abdominal aortic aneurysms, the detection of NGAL in serum might be affected. Still further, as indicated in Devarajan et al. (2010), *Biomark Med.*, 4:265-280, NGAL in urine might be susceptible to coexisting variables such as chronic kidney diseases, IgA nephropathy, lupus nephritis, and urinary tract infection.

The correlation between expression levels of microRNAs (miRNAs) and AKI was investigated in several studies. For instance, it was found that the expression levels of miR-24, miR-127, and miR-494 in the ischemia-reperfusion injury (IRI)-induced AKI mouse model are enhanced, and that miR-127 and miR-494 can be expected to serve as biomarkers for diagnosing AKI (see Lorenzen et al. (2014), *J. Am. Soc. Nephrol.*, 25:2717-2719; Aguado-Fraile et al. (2012), *PLoS One*, 7:e44305; and Yi-Fan et al. (2010), *J. Am. Soc. Nephrol.*, 23:2012-2023). In addition, as reported in Cui et al. (2016), *PeerJ.*, 4:e1729, the expression level of miR-214 is also increased in the AKI mouse model.

SUMMARY

According to one aspect of the present disclosure, a method for determining whether a human subject with acute myocardial infarction (AMI) is at the risk of developing acute kidney injury (AKI) includes:

obtaining a blood sample from the human subject;

determining at least two miRNA expression levels in the blood sample, the at least two miRNA expression levels being selected from the group consisting of an miR-23a-3p expression level, an miR-24-3p expression level, and an miR-145-5p expression level;

calculating probability of developing AKI from AMI based on the at least two miRNA expression levels and a logistic regression model, values of the at least two miRNA expression levels serving as inputs for the logistic regression model;

comparing the probability with a predetermined standard; and determining that the human subject is at the risk of developing AKI when the probability is higher than the predetermined standard.

According to another aspect of the present disclosure, a method for determining the risk of developing AKI in a human subject with AMI and inhibiting such development includes:

obtaining a blood sample from the human subject;

determining at least two miRNA expression levels in the blood sample, the at least two miRNA expression levels being selected from the group consisting of an miR-23a-3p expression level, an miR-24-3p expression level, and an miR-145-5p expression level;

calculating probability of developing AKI from AMI based on the at least two miRNA expression levels and a logistic regression model, values of the at least two miRNA expression levels serving as inputs for the logistic regression model;

comparing the probability with a predetermined standard;

determining that the human subject is at the risk of developing AKI when the probability is higher than the predetermined standard; and administering to the human subject at the risk of developing AKI an effective amount of a composition for inhibiting development of AKI.

DETAILED DESCRIPTION

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which this disclosure belongs. One skilled in the art will recognize many methods and materials similar or equivalent to those described herein, which could be used in the practice of this disclosure. Indeed, this disclosure is in no way limited to the methods and materials described.

As used herein, the terms "diagnose", "diagnosis" or "diagnosing" refer to distinguishing or identifying a disease, syndrome or condition or distinguishing or identifying a person having a particular disease, syndrome or condition. In illustrative embodiments of the present disclosure, assays and algorithms are used to diagnose whether a subject with acute myocardial infarction (AMI) is at the risk of developing acute kidney injury (AKI) based on an analysis of a sample.

Through research, the applicant surprisingly found that each of miR-23a-3p, miR-24-3p and miR-145-5p can serve as a reliable biomarker for determining whether a patient with AMI is likely to develop AKI, and that any two or all three of these miRNAs in combination can provide an even better result for such AKI determination.

Accordingly, the present disclosure provides a method for determining whether a human subject with AMI is at the risk of developing AKI, which comprises:

obtaining a blood sample from the human subject;

determining a microRNA (miRNA) expression level in the blood sample, the miRNA expression level being selected from the group consisting of an miR-23a-3p expression level, an miR-24-3p expression level, an miR-145-5p expression level, and combinations thereof;

comparing the miRNA expression level with a predetermined standard; and determining that the human subject is at the risk of developing AKI when the miRNA expression level is lower than the predetermined standard.

In an exemplary embodiment of the present disclosure, the miRNA expression level is the miR-23a-3p expression level. In another exemplary embodiment of the present disclosure, the miRNA expression level is the miR-24-3p expression level. In still another embodiment of the present disclosure, the miRNA expression level is the miR-145-5p expression level.

As used herein, the terms "miR-23a-3p", "miR-24-3p", and "miR-145-5p" are interchangeable with "hsa-miR-23a-3p", "hsa-miR-24-3p", and "hsa-miR-145-5p", respectively.

According to the present disclosure, diagnosis of AMI may be conducted using any well-known and commonly used method in the art according to well-recognized diagnosis criteria. In an exemplary embodiment of the present disclosure, diagnosis of AMI is conducted according to the criteria defined in Thygesen et al. (2007), *Eur. Heart J.*, 28:2528-2538.

According to the present disclosure, the blood sample may be collected from the human subject at any time of a suitable day. In an exemplary embodiment of the present disclosure, the blood sample is obtained from the human subject during a time period of a suitable day which ranges from 5:00 AM to 8:00 AM.

According to the present disclosure, before the step of determining the miRNA expression level, the blood sample may be subjected to a separation process, so that serum is separated therefrom and is used for the step of determining the miRNA expression level. In an exemplary embodiment, the separation process is a centrifugation process.

According to the present disclosure, the miRNA expression level may be determined using a method well-known to those skilled in the art. For example, the applicable method may be found in Chen et al. (2005), *Nucleic Acids Res.*, 33:e179 and Tian et al. (2015), *Org. Biomol. Chem.*, 13:2226-2238. In certain embodiments, the miRNA expression level may be determined using at least one of the following methodologies: polymerase chain reaction (PCR), real time PCR (also known as quantitative PCR (q-PCR)), reverse transcription PCR (RT-PCR), quantitative RT-PCR (RT-qPCR), hybridization, probe hybridization and gene expression array. The operating conditions and selection of reagents for these methodologies are within the expertise and routine skills of those skilled in the art. In one embodiment of the present disclosure, the miRNA expression level is determined using q-PCR.

According to the present disclosure, the term "predetermined standard" used in the step of comparison with the miRNA expression level may indicate a range, a value or a cut-off value for an miRNA expression level in a blood sample of a human individual with AMI who is considered as not developing AKI after monitoring. The cut-off value can be determined using a technique well-known to those skilled in the art.

As used herein, the term "human individual with AMI who is considered as not developing AKI after monitoring" refers to an individual with AMI who is not at the risk of developing AKI, i.e. an individual who has been subjected to monitoring (for instance, monitoring of the serum creatinine level) for a suitable time period after being diagnosed with AMI by a professional medical practitioner, and who is considered as not developing AKI after the monitoring. In an exemplary embodiment of the present disclosure, the suitable time period is 7 days.

According to the present disclosure, the risk of developing AKI from AMI may also be determined based on a combined cut-off value of any two or all three of the determined miR-23a-3p, miR-24-3p, and miR-145-5p expression levels. In certain embodiments, the combined cut-off value may be calculated by an equation formulated using statistical analysis (such as discriminant function analysis, logistic regression analysis, receiver operating characteristic curve analysis and ridge regression analysis).

Besides analyzing the correlation between the expression level of a single miRNA (miR-23a-3p, miR-24-3p, or miR-145-5p) and the risk of developing AKI from AMI, the applicant further investigated whether a combination of at least two of the miR-23a-3p, miR-24-3p, and miR-145-5p expression levels is applicable in determining the risk of developing AKI from AMI. Specifically, the applicant established logistic regression models based on different combinations of these miRNAs to calculate the probability values of the human subjects in each of the AMI$^+$AKI$^-$ and AMI$^+$AKI$^+$ groups regarding the development of AKI from AMI.

The results of the aforesaid investigation are as follows. Regarding the probability values calculated based on either any two or all three of the miR-23a-3p, miR-24-3p, and miR-145-5p expression levels in combination, the AMI$^+$AKI$^+$ group was always significantly higher than the AMI$^+$AKI$^-$ group. Furthermore, via ROC curve analysis, it was found that the AUC obtained based on the respective combination of miRNA expression levels is higher than that obtained based on a single miRNA expression level.

Accordingly, the present disclosure provides a method for determining whether a human subject with AMI is at the risk of developing AKI, which comprises:

obtaining a blood sample from the human subject;

determining at least two miRNA expression levels in the blood sample, the at least two miRNA expression levels being selected from the group consisting of an miR-23a-3p expression level, an miR-24-3p expression level, and an miR-145-5p expression level;

calculating probability of developing AKI from AMI based on the at least two miRNA expression levels and a logistic regression model, values of the at least two miRNA expression levels serving as inputs for the logistic regression model;

comparing the probability with a predetermined standard; and determining that the human subject is at the risk of developing AKI when the probability is higher than the predetermined standard.

In an exemplary embodiment of the present disclosure, the at least two miRNA expression levels are the miR-23a-3p and miR-24-3p expression levels, and the logistic regression model is represented by the following formula (I):

$$\text{logit}[\Pr(Y=1)]=13.962+(0.982\times A)-(1.987\times B) \quad (I)$$

where "logit[Pr(Y=1)]" represents the probability that the human subject will develop AKI from AMI, "A" represents the miR-23a-3p expression level ($C_t$), and "B" represents the miR-24-3p expression level ($C_t$).

In another exemplary embodiment of the present disclosure, the at least two miRNA expression levels are the miR-24-3p and miR-145-5p expression levels, and the logistic regression model is represented by the following formula (II):

$$\text{logit}[\Pr(Y=1)]=17.11-(1.984\times C)+(0.901\times D) \quad (II)$$

where "logit[Pr(Y=1)]" represents the probability that the human subject will develop AKI from AMI, "C" represents the miR-24-3p expression level ($C_t$), and "D" represents the miR-145-5p expression level ($C_t$).

In still another embodiment of the present disclosure, the at least two miRNA expression levels are the miR-23a-3p, miR-24-3p and miR-145-5p expression levels, and the logistic regression model is represented by the following formula (III):

$$\text{logit}[\Pr(Y=1)]=17.12+(0.742\times E)-(2.558\times F)+(0.772\times G) \quad (III)$$

where "logit[Pr(Y=1)]" represents the probability that the human subject will develop AKI from AMI, "E" represents the miR-23a-3p expression level ($C_t$), "F" represents the miR-24-3p expression level ($C_t$), and "G" represents the miR-145-5p expression level ($C_t$).

According to the present disclosure, diagnosis of AMI, the collection and processing of the blood sample, and the determination of the miRNA expression levels are as described above.

According to the present disclosure, the term "predetermined standard" used in the aforesaid step of comparison with the probability may indicate a range, a value or a cut-off value for probability of developing AKI with respect to a human individual with AMI who is considered as not developing AKI after monitoring. The cut-off value can be determined using a technique well-known to those skilled in the art.

Based on the satisfactory diagnostic power of miR-23a-3p, miR-24-3p, and miR-145-5p (alone or in combination) for determining the risk of developing AKI from AMI, the present disclosure further provides a kit for determining whether a human subject with AMI is at the risk of developing AKI, which comprises:

at least one reagent for determining at least one miRNA expression level, the at least one miRNA expression level being selected from the group consisting of an miR-23a-3p expression level, an miR-24-3p expression level, and an miR-145-5p expression level; and instructions for using the kit in any one of the two aforesaid methods.

According to the present disclosure, if it is determined that the human subject with AMI is at the risk of developing AKI, the following step of inhibiting development of AKI may be used in combination with the steps in any one of the two aforesaid methods: administering to the human subject at the risk of developing AKI from AMI an effective amount of a composition for inhibiting development of AKI. Therefore, the present disclosure also provides a method for determining the risk of developing AKI from AMI and inhibiting such development.

According to the present disclosure, the composition for inhibiting development of AKI may comprise an ingredient well-known in the art, and hence is only briefly described herein.

In certain embodiments, the composition for inhibiting development of AKI is a pharmaceutical composition which comprises an active ingredient selected from the group consisting of a vasopressor, an antioxidant, an HMG-CoA (3-hydroxy-3-methyl-glutaryl-coenzyme A) reductase inhibitor, and combinations thereof.

According to the present disclosure, the antioxidant may be selected from the group consisting of N-acetylcysteine, sodium bicarbonate, ascorbic acid, and combinations thereof. In some embodiments, the antioxidant is N-acetylcysteine. In other embodiments, the antioxidant is sodium bicarbonate.

According to the present disclosure, the HMG-CoA reductase inhibitor may be a statin. In certain embodiments, the statin is a simvastatin.

According to the present disclosure, the composition for inhibiting development of AKI is for intravascular volume expansion, and may be a fluid for such purpose. In certain embodiments, the composition for inhibiting development of AKI is an intravenous infusion solution which comprises an ingredient selected from albumin, colloid, and crystalloid. In an exemplary embodiment, the intravenous infusion solution comprises isotonic crystalloid.

In certain circumstances, N-acetylcysteine and isotonic crystalloid may be administered together respectively through oral and intravenous routes to enhance the therapeutic effect.

The present disclosure will be described in more detail with reference to the following examples, which are given for the purpose of illustration only and are not intended to limit the scope of the present disclosure.

EXAMPLES

Test Subjects:

The test subjects participating in the study below were recruited under a protocol approved by the Chang Gung Medical Foundation Institutional Review Board. Exclusion criteria were applied to exclude any patient who was younger than 20 years old, who had end stage renal failure and received long-term dialysis treatment, and who had been hospitalized for less than 24 hours or had been repeatedly hospitalized.

A total of 49 human subjects served as the test subjects in the study below, and were patients that were diagnosed with acute myocardial infarction (AMI) by the Chang Gung Memorial Hospital, Department of Internal Medicine, Cardiovascular Division during the period from November of 2009 to December of 2014, and that were admitted to the Coronary Care Unit of the Chang Gung Memorial Hospital. Informed consent was obtained from each of the test subjects.

From the first day when the respective one of the test subjects was admitted to the Coronary Care Unit, a serum sample of the respective test subject was regularly collected. Furthermore, the serum creatinine level measured was used to determine whether the respective test subject was developing acute kidney injury (AKI), according to the Clinical Practice Guidelines for AKI proposed by the organization "Kidney Disease: Improving Global Outcomes" (KDIGO). Specifically, when the serum creatinine level increased by 0.3 mg/dL or more within two days compared to that measured on the first day, or when the serum creatinine level increased 1.5 fold or more within seven days compared to that measured on the first day, the respective test subject was diagnosed as developing AKI. Within the first 7 days of admission to the Coronary Care Unit, 23 out of the 49 test subjects developed AKI and were classified as an $AMI^+AKI^+$ group. The remaining 26 test subjects were classified as an $AMI^+AKI^-$ group. The clinical information of the test subjects in the $AMI^+AKI^-$ and $AMI^+AKI^+$ groups is shown in Table 1 below.

TABLE 1

Clinical information of test subjects in $AMI^+AKI^-$ and $AMI^+AKI^+$ groups

| Group | $AMI^+AKI^-$ | $AMI^+AKI^+$ |
|---|---|---|
| Number of test subjects | 26 | 23 |
| Age[a] | 59 ± 2 | 73 ± 2 |
| Gender (Number of female/number of male) | 4/22 | 4/19 |
| Weight (kg)[a] | 68.9 ± 2.6 | 65.3 ± 2.3 |
| Serum creatinine level (mg/dL)[a,b] | 0.9 ± 0.1 | 3.4 ± 0.5 |

[a]Mean ± standard deviation (S.D.)
[b]The highest value within first 7 days of admission to Coronary Care Unit General Procedures:

1. Preparation of Serum Sample

Blood collected from the respective test subject was subjected to centrifugation at 4° C. and 2,000 rpm for 10 minutes, followed by collecting the resulting supernatant, i.e. a serum sample. The serum sample thus obtained was subjected to cryogenic storage at −80° C. for further use.

2. Statistical Analysis

In the following example, each statistical analysis was conducted using IBM SPSS Statistics 22 (SPSS Inc., IL, USA). The difference between the two groups was assessed by virtue of nonparametric Mann-Whitney U test. Statistical significance is indicated by $p<0.05$.

Example 1. Evaluation for Correlation Between miRNA Expression Levels in Serum and AMI Patients' Risk of Developing AKI A. Evaluation for Correlation Between Expression Level of Single miRNA and Risk of Developing AKI from AMI In this study, on the first day from the beginning of admission to the Coronary Care Unit (namely, before the onset of AKI), the expression levels of miR-23a-3p, miR-24-3p, miR-127-3p, miR-145-5p, miR-214-3p, and miR-494-3p in serum were determined for each of the test subjects in the $AMI^+AKI^-$ and $AMI^+AKI^+$ groups, so that whether the development of AKI can be predicted based on the expression level of each of these miRNAs was evaluated.

First of all, the serum sample obtained from the respective test subject on the first day from the beginning of admission to the Coronary Care Unit was subjected to centrifugation at 12,000 rpm for 5 minutes so as to remove cell debris. Subsequently, 250 μL of the resulting supernatant was mixed with 1,000 μL of QIAzol Lysis Reagent (Qiagen) and $10^7$ copies of synthetic cel-miR-39-3p (IDT, Coralville, Iowa) which served as a spike-in control. Extraction of total RNAs was conducted using miRNeasy Mini Kit (Qiagen) according to the manufacturer's instructions. Afterward, the concentration of total RNAs was determined using Quant-iT™ RiboGreen® RNA Assay Kit (Invitrogen) and NanoDrop 3300 Fluorospectrophotometer (Thermo Scientific, DE, USA) according to the manufacturer's instructions.

5.4 μL of the total RNAs thus obtained were evenly mixed with 40 U RNaseOUT Recombinant Ribonuclease Inhibitor (Thermo Fisher Scientific), 1×PCR (polymerase chain reaction) Buffer, and 2.5 mM $MgCl_2$. 0.5 U heparinase I (Sigma-Aldrich, MO, USA) was added to the resulting mixture, followed by conducting incubation at 25° C. for 1 hour to eliminate the interference by heparin. A reverse transcription reaction was conducted using TaqMan® MicroRNA Reverse Transcription Kit and TaqMan® MicroRNA Assays (Applied Biosystems, CA, USA) according to the manufacturer's instructions, so as to synthesize first-strand cDNAs.

Subsequently, the thus obtained first-strand cDNAs which served as templates, TaqMan® MicroRNA Assays, and QuantStudio™ 12K Flex Real-Time PCR system (Applied Biosystems, CA, USA) were used to conduct quantitative PCR (q-PCR) according to the manufacturer's instructions. The operation conditions of q-PCR are shown in Table 2, and the TaqMan® MicroRNA Assay Mix for the respective one of miRNAs is shown in Table 3.

TABLE 2

Reaction conditions of q-PCR

| Contents | Volume (μL) |
|---|---|
| 5-fold diluted first strand cDNAs | 0.5 |
| TaqMan ® MicroRNA Assay Mix (Applied Biosystems) | 3.5 |
| TaqMan ® 2X Universal PCR Master Mix (Applied Biosystems) | 4 |

Operating conditions: Pre-incubation at 95° C. for 10 minutes, followed by 40 cycles of the following reactions: denaturation at 95° C. for 15 seconds, and primer annealing and elongation at 60° C. for 60 seconds.

TABLE 3

TaqMan ® MicroRNA Assay Mix for respective one of miRNAs

| miRNA | Assay ID of TaqMan ® MicroRNA Assay Mix |
|---|---|
| miR-23a-3p (corresponding to miRBase accession number MIMAT0000078) | 000399 |
| miR-24-3p (corresponding to miRBase accession number MIMAT0000080) | 000402 |
| miR-127-3p (corresponding to miRBase accession number MIMAT0000446) | 000452 |
| miR-145-5p (corresponding to miRBase accession number MIMAT0000437) | 002278 |

TABLE 3-continued

TaqMan ® MicroRNA Assay Mix for respective one of miRNAs

| miRNA | Assay ID of TaqMan ® MicroRNA Assay Mix |
|---|---|
| miR-214-3p (corresponding to miRBase accession number MIMAT0000271) | 002306 |
| miR-494-3p (corresponding to miRBase accession number MIMAT0002816) | 002365 |
| cel-miR-39-3p (corresponding to miRBase accession number MIMAT0000010) | 000200 |

The PCR product obtained via the respective miRNA was detected by virtue of fluorescence of FAM™ dye, and the cycle threshold ($C_t$) value was calculated. Afterward, normalization was conducted using comparative $C_t$ method based on the $C_t$ value of the PCR product obtained via cel-miR-39, so as to correct operational errors. Further, the concentration of total RNAs in the respective serum sample measured previously was subjected to normalization to correct the concentration difference between different serum samples, so as to calculate the expression level ($C_t$) of the respective miRNA.

Receiver operating characteristic (ROC) curve analysis was applied to evaluate whether the expression level of the respective miRNA can serve as an excellent basis for diagnosis and discriminate between the test subjects in the AMI$^+$AKI$^-$ and AMI$^+$AKI$^+$ groups. Further, Youden's index analysis was used to determine the optimal cut-off value. The results thus obtained are shown in Tables 4 and 5 below.

As shown in Tables 4 and 5, the miR-23a-3p, miR-24-3p, and miR-145-5p expression levels of the AMI$^+$AKI$^+$ group were significantly lower than those of the AMI$^+$AKI$^-$ group, respectively. However, regarding each of the miR-127-3p, miR-214-3p, and miR-494-3p expression levels, there was no significant difference between the AMI$^+$AKI$^+$ group and the AMI$^+$AKI$^-$ group. These results indicate that each of miR-23a-3p, miR-24-3p, and miR-145-5p can serve as a biomarker suitable for predicting whether a patient with AMI will develop AKI, but each of miR-127-3p, miR-214-3p, and miR-494-3p is not an optimal biomarker for predicting development of AKI in AMI patients.

When the risk of developing AKI from AMI was determined based on the cut-off value of the respective one of the miR-23a-3p, miR-24-3p, and miR-145-5p expression levels (specifically, the test subject, who had the respective miRNA expression level lower than the cut-off value, was considered as being likely to develop AKI), the diagnostic specificity of miR-23a-3p was up to 92.31%, and the diagnostic sensitivities of miR-24-3p and miR-145-5p were respectively up to 82.61% and 86.96%. In addition, AUC values of the miR-23a-3p, miR-24-3p, and miR-145-5p expression levels were 0.801, 0.828, and 0.763, respectively, revealing that each of miR-23a-3p, miR-24-3p, and miR-145-5p is a satisfactory biomarker for determining the risk of developing AKI from AMI.

B. Evaluation for Correlation Between Expression Levels of Plurality of miRNAs in Combination and Risk of Developing AKI from AMI In order to investigate whether a combination of at least two of miR-23a-3p, miR-24-3p, and miR-145-5p can further improve the diagnostic power in determining the risk of developing AKI from AMI, the logistic regression models for different combinations of these miRNAs were established. The formulae used to calculate the AMI patients'

TABLE 4

Results of ROC curve analysis and cut-off values for miR-23a-3p, miR-24-3p, and miR-145-5p

| miRNA | Expression Level ($C_t$)$^a$ | | p-value | Cut-off value | Sensitivity (%) | Specificity (%) | UC |
|---|---|---|---|---|---|---|---|
| | AMI$^+$AKI$^-$ group | AMI$^+$AKI$^+$ group | | | | | |
| miR-23a-3p | 12.23 ± 0.28 | 10.59 ± 0.32 | <0.001 | <10.89 | 60.87 | 92.31 | .801 |
| miR-24-3p | 13.64 ± 0.26 | 11.74 ± 0.31 | <0.001 | <12.99 | 82.61 | 69.23 | .828 |
| miR-145-5p | 9.70 ± 0.31 | 8.16 ± 0.29 | 0.002 | <9.67 | 86.96 | 53.85 | .763 |

$^a$Mean ± S.D.

TABLE 5

Results of ROC curve analysis for miR-127-3p, miR-214-3p, and miR-494-3p

| miRNA | Expression Level ($C_t$)$^a$ | | p-value | AUC |
|---|---|---|---|---|
| | AMI$^+$AKI$^-$ group | AMI$^+$AKI$^+$ group | | |
| miR-127-3p | 4.96 ± 0.55 | 4.22 ± 0.36 | 0.279 | 0.590 |
| miR-214-3p | 6.76 ± 0.29 | 6.31 ± 0.27 | 0.173 | 0.614 |
| miR-494-3p | 3.05 ± 0.42 | 2.25 ± 0.38 | 0.147 | 0.620 |

$^a$Mean ± S.D.

probability of developing AKI (i.e. logit[Pr(Y=1)], where Y=1 indicates that a patient with AMI will develop AKI) are shown below.

The following formula (I) was established based on the combination of miR-23a-3p and miR-24-3p:

$$\text{logit}[Pr(Y=1)]=13.962+(0.982\times A)-(1.987\times B) \quad (I)$$

where: A=miR-23a-3p expression level ($C_t$)
B=miR-24-3p expression level ($C_t$)

The following formula (II) was established based on the combination of miR-24-3p and miR-145-5p:

$$\text{logit}[Pr(Y=1)]=17.11-(1.984\times C)+(0.901\times D) \quad (II)$$

where: C=miR-24-3p expression level ($C_t$)
D=miR-145-5p expression level ($C_t$)

The following formula (III) was established based on the combination of miR-23a-3p, miR-24-3p, and miR-145-5p:

$$\text{logit}[\Pr(Y=1)]=17.12+(0.742 \times E)-(2.558 \times F)+(0.772 \times G) \quad \text{(III)}$$

where: E=miR-23a-3p expression level ($C_t$)
F=miR-24-3p expression level ($C_t$)
G=miR-145-5p expression level ($C_t$)

In addition, the results of ROC curve analysis and the cut-off values for the different miRNA combinations are shown in Table 6 below.

TABLE 6

Results of ROC curve analysis and cut-off values for different combinations of miR-23a-3p, miR-24-3p, and miR-145-5p

| miRNA combination | Probability[a] AMI⁺AKI⁻ group | Probability[a] AMI⁺AKI⁺ group | p-value | Cut-off value | Sensitivity (%) | Specificity (%) | UC |
|---|---|---|---|---|---|---|---|
| miR-23a-3p + miR-24-3p | 0.30 ± 0.04 | 0.66 ± 0.06 | <0.001 | >0.46 | 73.91 | 80.77 | .838 |
| miR-24-3p + miR-145-5p | 0.29 ± 0.04 | 0.67 ± 0.06 | <0.001 | >0.54 | 69.57 | 88.46 | .843 |
| miR-23a-3p + miR-24-3p + miR-145-5p | 0.29 ± 0.04 | 0.67 ± 0.06 | <0.001 | >0.30 | 95.65 | 65.38 | .853 |

[a]Mean ± S.D.

As shown in Table 6, based on either the combination of any two miRNAs or the combination of all three miRNAs, the probability of developing AKI determined for the AMI⁺AKI⁺ group was significantly higher than that determined for the AMI⁺AKI⁻ group. Moreover, when the risk of developing AKI from AMI was determined based on the cut-off value of the probability of the respective miRNA combination (specifically, the test subject, who had the probability of the respective miRNA combination higher than the cut-off value, was considered as being likely to develop AKI), each AUC thus obtained was higher than AUC obtained based on a single miRNA. In particular, the combination of all three of miR-23a-3p, miR-24-3p, and miR-145-5p reached the highest diagnostic sensitivity (95.65%). These results indicate that the combination of any two or all three of miR-23a-3p, miR-24-3p, and miR-145-5p can exhibit a synergistic effect and hence provide a better diagnostic power in determining the risk of developing AKI from AMI, compared to any single one of these miRNAs.

All patents and literature references cited in the present specification as well as the references described therein, are hereby incorporated by reference in their entirety. In case of conflict, the present description, including definitions, will prevail.

While this disclosure has been described in connection with specific embodiments thereof, it will be understood that it is capable of further modifications and this application is intended to cover any variations, uses, or adaptations of the disclosure following, in general, the principles of the disclosure and including such departures from the present customary practice within the art to which the disclosure pertains and as may be applied to the essential features hereinbefore set forth, and as follows in the scope of the appended claims.

What is claimed is:

1. A method for determining a risk of developing acute kidney injury (AKI) in a human subject with acute myocardial infarction (AMI) and inhibiting such development, the method comprising:
   obtaining a blood sample from the human subject;
   determining at least two miRNA expression levels in the blood sample, the at least two miRNA expression levels being selected from the group consisting of an miR-23a-3p expression level, an miR-24-3p expression level, and an miR-145-5p expression level;
   calculating probability of developing AKI from AMI based on the at least two miRNA expression levels and a logistic regression model, wherein values of the at least two miRNA expression levels are inputted into the logistic regression model;
   comparing the probability with a predetermined standard;
   determining that the human subject is at the risk of developing AKI when the probability is higher than the predetermined standard; and
   administering to the human subject at the risk of developing AKI an effective amount of a composition for inhibiting development of AKI.

2. The method of claim 1, wherein the composition for inhibiting development of AKI is a pharmaceutical composition which comprises an active ingredient selected from the group consisting of a vasopressor, an antioxidant, an 3-hydroxy-3-methyl-glutaryl-coenzyme A reductase inhibitor, and combinations thereof.

3. The method of claim 1, wherein the at least two miRNA expression levels are the miR-23a-3p and miR-24-3p expression levels.

4. The method of claim 3, wherein the logistic regression model is represented by the following formula (I):

$$\text{logit}[\Pr(Y=1)]=13.962+(0.982 \times A)-(1.987 \times B) \quad \text{(I)}$$

where logit [Pr(Y=1)] represents the probability of developing AKI from AMI, A represents a cycle threshold value of the miR-23a-3p expression level, and B represents a cycle threshold value of the miR-24-3p expression level.

5. The method of claim 1, wherein the at least two miRNA expression levels are the miR-24-3p and miR-145-5p expression levels.

6. The method of claim 5, wherein the logistic regression model is represented by the following formula (II):

$$\text{logit}[\Pr(Y=1)]=17.11-(1.984 \times C)+(0.901 \times D) \quad \text{(II)}$$

where logit [Pr(Y=1)] represents the probability of developing AKI from AMI, C represents a cycle threshold value of the miR-24-3p expression level, and D represents a cycle threshold value of the miR-145-5p expression level.

7. The method of claim 1, wherein the at least two miRNA expression levels are the miR-23a-3p, miR-24-3p and miR-145-5p expression levels.

8. The method of claim 7, wherein the logistic regression model is represented by the following formula (III):

$$\text{logit}[Pr(Y=1)] = 17.12 + (0.742 \times E) - (2.558 \times F) + (0.772 \times G) \quad \text{(III)}$$

where logit [Pr(Y=1)] represents the probability of developing AKI from AMI, E represents a cycle threshold value of the miR-23a-3p expression level, F represents a cycle threshold value of the miR-24-3p expression level, and G represents a cycle threshold value of the miR-145-5p expression level.

9. The method of claim 1, wherein the blood sample is serum.

10. The method of claim 9, wherein the at least two miRNA expression levels are determined using at least one of the following methodologies: polymerase chain reaction (PCR), real time PCR, reverse transcription PCR, quantitative RT-PCR, hybridization, probe hybridization, and gene expression array.

* * * * *